United States Patent
Poon et al.

(10) Patent No.: US 10,111,722 B2
(45) Date of Patent: Oct. 30, 2018

(54) ROBOTIC SYSTEM

(71) Applicant: THE CHINESE UNIVERSITY OF HONG KONG, Hong Kong (CN)

(72) Inventors: Chung Yan Carmen Poon, Hong Kong (CN); Wai Yan Philip Chiu, Hong Kong (CN); Yeung Yam, Hong Kong (CN); Yun Wong James Lau, Hong Kong (CN); Ka Chun Lau, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 296 days.

(21) Appl. No.: 14/928,971

(22) Filed: Oct. 30, 2015

(65) Prior Publication Data

US 2016/0166343 A1    Jun. 16, 2016

Related U.S. Application Data

(60) Provisional application No. 62/072,603, filed on Oct. 30, 2014.

(51) Int. Cl.
| | |
|---|---|
| *A61B 17/00* | (2006.01) |
| *A61B 34/37* | (2016.01) |
| *A61B 34/30* | (2016.01) |
| *A61B 18/00* | (2006.01) |
| *A61B 18/14* | (2006.01) |

(52) U.S. Cl.
CPC .... *A61B 34/37* (2016.02); *A61B 2017/00269* (2013.01); *A61B 2017/00867* (2013.01);
(Continued)

(58) Field of Classification Search
CPC .......... A61B 2017/00269; A61B 34/37; A61B 2034/301; A61B 2034/305; A61B 2034/306
See application file for complete search history.

(56) References Cited

U.S. PATENT DOCUMENTS

| | | | |
|---|---|---|---|
| 8,882,660 B2 | 11/2014 | Phee et al. | |
| 2002/0082584 A1* | 6/2002 | Rosenman | A61M 25/0014 604/523 |

(Continued)

FOREIGN PATENT DOCUMENTS

| | | |
|---|---|---|
| CN | 102802551 A | 11/2012 |
| CN | 103025225 A | 4/2013 |

OTHER PUBLICATIONS

Poon et al., "A Bio-Inspired Flexible Robot with Hybrid Actuation Mechanisms for Endoscopic Surgery," pp. 81-82.
(Continued)

*Primary Examiner* — Ashley Fishback
(74) *Attorney, Agent, or Firm* — Knobbe, Martens, Olson & Bear, LLP

(57) ABSTRACT

The present invention discloses a task specific robot for the procedure of endoscopic submucosal dissection (ESD). This robot has two arms with nine degrees of freedom (DOF), and the capability of tissue elevation and dissection. An optimal design of these robot arms requires the use of shape memory alloy (SMA) wire and steel wire actuators to develop an improved actuation mechanism, which enables force to be transmitted to the distal tip of the robot arms for an efficient tissue elevation and dissection.

21 Claims, 5 Drawing Sheets

(52) U.S. Cl.
CPC ........... *A61B 2018/00595* (2013.01); *A61B 2018/1412* (2013.01); *A61B 2034/301* (2016.02); *A61B 2034/306* (2016.02); *A61B 2218/002* (2013.01); *A61B 2218/007* (2013.01)

(56) References Cited

U.S. PATENT DOCUMENTS

| | | | | |
|---|---|---|---|---|
| 2005/0272977 | A1* | 12/2005 | Saadat | A61B 1/0008 600/114 |
| 2010/0331856 | A1* | 12/2010 | Carlson | A61B 1/00147 606/130 |
| 2012/0078053 | A1 | 3/2012 | Phee et al. | |
| 2013/0338433 | A1 | 12/2013 | Goldman et al. | |
| 2014/0135793 | A1 | 5/2014 | Cooper et al. | |
| 2017/0112583 | A1* | 4/2017 | Cohen | A61B 90/50 |

OTHER PUBLICATIONS

Xu et al., "A Feed-forward Friction Compensation Motion Controller for a Tendon-Sheath-Driven Flexible Robotic Gripper"; Proceeding of the IEEE International Conference on Robotics and Biomimetics (ROBIO), Shenzhen, China, Dec. 2013, pp. 2112-2117.

Lau et al., "A Flexible Surgical Robotic System for Removal of Early-Stage Gastrointestinal Cancers by Endoscopic Submucosal Dissection"; Citation Information: DOI 10.1109/TII.2016.2576960, IEEE Transactions on Industrial Informatics, published on Jun. 7, 2016, in IEEE Transactions on Industrial Informatics (vol. PP, Issue 99)11 pages.

Poon et al., "A Novel User-Specific Wearable Controller for Surgical Robots"; Springer International Publishing Switzerland 2015, Editor: A. Marcus; DUXU 2015, Part III, LNCS 9188, pp. 693-701, 2015. DOI: 10.1007/978-3-319-20889-3_64.

Lau et al., "Design and Development of a Task Specific Robot for Endoscopic Submucosal Dissection of Early Gastrointestinal Cancers"; 2014 International Symposium on Optomechatronic Technologies; 978-1-4799-6666-0/14 $31.00; 2014 IEEE; DOI 10.1109/ISOT.2014.57.

Lau et al., "Motion Compensation of Tendon-Sheath Driven Continuum Manipulator for Endoscopic Surgery"; MATEC Web of Conferences, 32.04007 (2015); DOI: 10.1051/matecconf/20153204007; Published by EDP Sciences, 2015, 6 pages.

* cited by examiner

ROBOTIC SYSTEM

TECHNICAL FIELD

The present application generally relates to a robotic system, more particularly, to a master-slave robotic system for use in Endoscopic Submucosal Dissection (ESD).

BACKGROUND

Gastric and colorectal cancers are the common types of cancer in different area of the world. They are also the top leading causes of cancer death. Gastrointestinal (GI) cancers grow from the mucosal layer. Survival rates for patients suffering from these cancers may be improved if pre-malignant and early cancers are removed en bloc at an early stage before they spread to lymph nodes.

Endoscopic mucosal resection (EMR) and Endoscopic submucosal dissection (ESD) were developed for removal of pre-malignant and early cancers in the GI tract. These procedures are performed with the use of a flexible endoscope and have advantages of being minimally invasive and organ sparing. To remove larger lesions, ESD, which is associated with a lower rate of local recurrence (compared to EMR) because of a higher rate of complete resection in a single piece, is usually required.

Generally, during an ESD surgery, the margins of the lesion are marked by electrocautery, and submucosal injection is used to lift the lesion; a circumferential incision into the submucosa is performed around the lesion with specialized endoscopic electrocautery knives; and the lesion is dissected from underlying deep layers of GI tract wall with the electrocautery knife and removed. Compared to open surgery, mucosal resection performed with an endoscope is clearly less invasive.

Although ESD effectively removes early gastric and colorectal cancers, ESD is a technically demanding procedure associated with a higher risk of complications. In general, ESD mainly has three shortcomings. First, the current flexible endoscopes have a single instrument channel. Endoscopists can only operate with a single accessory at a time. Second, it is difficult to maintain the tip of a flexible endoscope in a stable position inside a hollow viscus. Targeting a mucosal lesion with a flexible endoscope can be technically challenging. Often incisions are made inadvertently resulting in major complications such as perforation and bleeding. Thirdly, large bowel ESD surgery located in the proximal large bowel (cecum and transverse colon) is more demanding to perform due to difficulty in maintaining the position of the endoscope and also a thinner muscle layer.

Surgical robots have been developed for many years. There are few robots which can be applied with the use of flexible endoscopes. Robots aim to simulate operating with two arms. This design is inspired by some animal's body structure such as human and lobster where they both use their arms and eyes to finish tasks. This design can reduce the learning curve of surgeon. Our previous work showed the preliminary design of our robot and the usability of this structure in doing ESD. Moreover, arm liked design mimics our wrists and provides more degree of freedom. This makes endoscopic dissection easier and more efficient. This concept is also adopted in our design of this robot.

The nowadays surgical robot can be divided into two categories: direct driven and motorized. The advantages of direct driven robot are low cost and simple structure. Controller and robot are connected directly by mechanical structures such as tendon and sheath. Operators control the robot through the controller. There is direct force feedback to the controller and then onto the operator. However, the drawback of direct driven robot is lack of control accuracy.

Pure mechanical structure usually has backlash and force losing problems. Robot performs different from the input of the controller. Motorized robot can solve the above problems. For example, compensatory mechanism can be used to cancel backlash and force reduction. In addition, motorized robot can have more degrees of freedom since the motion of the robot is not directly mapped with the controller. The motion of the robot can be more complex.

The current endoscopic robots have structural limitations that robot arms are embedded in the endoscope platform. When surgeon is inserting the robot into patents gastrointestinal tract, the robot arms at the tip are bulky and thus it will be difficult for them to be passed. They can potentially cause mucosal damage as they are pushed along the digestive tract. Beside the robots having a cap to protect the robot arm, the endoscope platform needs to be developed together with the robot. The cost is therefore increased.

SUMMARY

According to an embodiment of the present application, disclosed is a robot for Endoscopic Submucosal Dissection (ESD). The robot comprises a slave device configured with a first arm and a second arm; an endoscopic platform with at least two channels extensible to a target tissue and for receiving the first and second arms, respectively; and a master device configured to control the first arm to retract the target tissue and control the second arm to dissect the retracted tissue.

In embodiments of the present application, each of the first arm and the second arm may comprise an identical continuum structure and an end-effector connected with the continuum structure, wherein the continuum structure is flexible to guide the end-effector to the target tissue.

In embodiments of the present application, each continuum structure may comprise a backbone configured to form a constant curvature, two pairs of actuators extensible along formed constant curvature and configured to drive the end-effector, and a plurality of guide discs separated from each other at a distance and having holes for receiving the actuators.

In embodiments of the present application, the actuators may be formed of combination of shape memory alloy and coated metal wire. This combination takes advantage of both merits. SMA can form curve which eases the kinematic modeling of continuum structure. Moreover, the superplastic SMA actuates the continuum structure with push-and-pull movement, which doubles the driving force compared with pulling mechanism, making downscale of the whole robotic structure possible. On the other hand, the coated metal wire is more flexible which can conform to irregular structure, such as the groove on gripper.

In embodiments of the present application, each of the actuators may be received in a coil sheath. The coil sheath serves as flexible channel, conveying force from motor drivers to the distal structure. Another function of using coil sheath is that it serves as a force turning mechanism. The sheaths for upper structures, like sheath for the gripper, are passed through the continuum structure, and therefore, the actuating force released by upper structure can distribute evenly along the sheath rather than cause unwanted deformation on the continuum part and thus protecting from self-destruction.

In embodiments of the present application, the end-effecter on the first arm may be a gripper, and the end-effecter on the second arm may be a dissector.

In one embodiments of the present application, the first arm may have at least 5 degree-of-freedom. In another embodiment of the present application, the second arm may have at least 4 degree-of-freedom.

The coil sheaths may be kept as a bundle and fixed inside a rubber tube, which serves as the flexible shaft of a single robot arm. There is no relative movement between the flexible shaft and sheaths inside. Thus, translation of the robotic arm is achieved by fastening the flexible shaft onto linear rack driven by motor.

In further aspect of the present application, disclosed is a robot for Endoscopic Submucosal Dissection (ESD), which may comprise: a first arm; a second arm; an endoscopic platform with at least two channels extensible to a target tissue and for receiving the first and second arms, respectively, wherein the first arm is configured to retract the target tissue and the second arm is configured to dissect the retracted tissue.

In embodiments of the present application, each of the first arm and the second arm may comprise an identical continuum structure and an end-effector connected with the continuum structure, wherein the continuum structure is flexible to guide the end-effector to the target tissue.

In embodiments of the present application, the continuum structure may comprise: a backbone for forming a constant curvature; two pairs of actuators extensible along formed constant curvature and configured to drive the end-effector; and a plurality of guide discs separated from each other at a distance and having holes for receiving the actuators.

BRIEF DESCRIPTION OF THE DRAWING

Exemplary non-limiting embodiments of the present invention are described below with reference to the attached drawings. The drawings are illustrative and generally not to an exact scale. The same or similar elements on different figures are referenced with the same reference numbers.

DETAILED DESCRIPTION

Reference will now be made in detail to exemplary embodiments, examples of which are illustrated in the accompanying drawings. When appropriate, the same reference numbers are used throughout the drawings to refer to the same or like parts.

Figure 1:
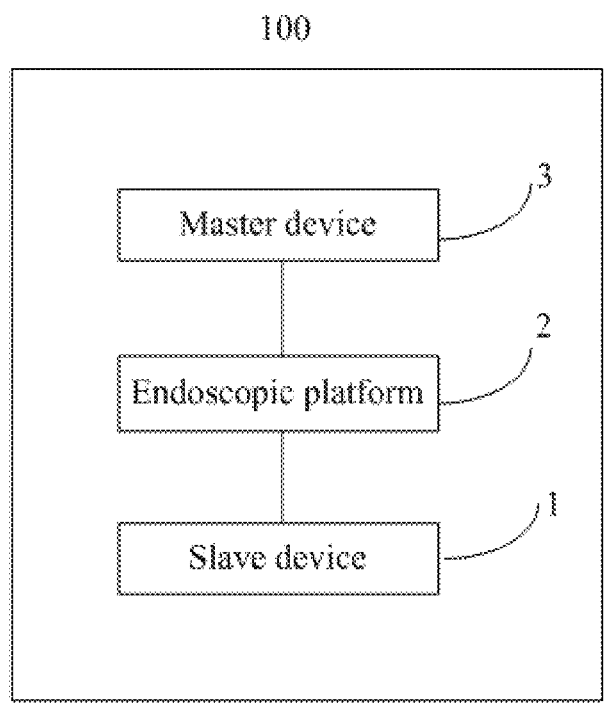
FIG. 1 is a block diagram illustrating a structure of a robot for use in ESD.

FIG. 1 is a block diagram of a robot 100 for Endoscopic Submucosal Dissection (ESD) according to an embodiment of the present application. The robot 100 comprises a slave device 1, an endoscopic platform 2, and a master device 3. The slave device 1 is configured with a first arm and a second arm. The endoscopic platform 2 has at least two channels extensible to a target tissue and for receiving the first and the second arms, respectively. The master device 3 is configured to control the first arm to retract the target tissue and control the second arm to dissect the retracted tissue. In some embodiments, the number of the channels can be varied as needed.

Figure 2:
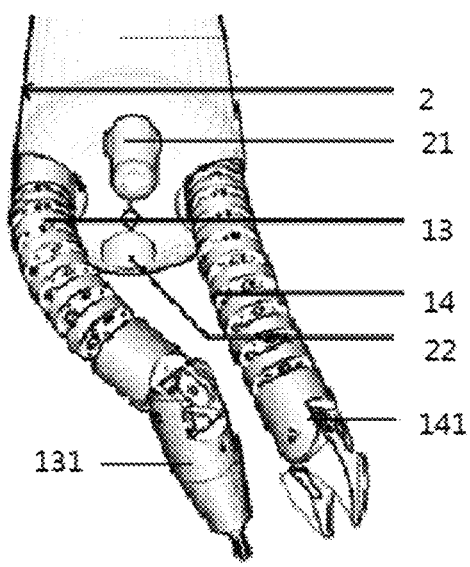
FIG. 2 is a schematic diagram illustrating a slave device and an endoscopic platform.

FIG. 2 shows the detailed configuration of the slave device 1. As shown in FIG. 2, the endoscopic platform 2 has four independent channels, i.e., upper, lower, left, and right channels, and the slave device 1 comprises two arms 13 and 14, one for tissue dissection and one for tissue retraction. Each of the arms 13, 14 comprises an identical continuum structure and an end-effector connected with the continuum structure, wherein the continuum structure is flexible to guide the end-effector to the target tissue. In this embodiment, a dissector 131 is attached to a distal end of the left arm 13 as an end-effector. In this embodiment, a gripper 141 is attached to the distal end of the left arm 13 as an end-effector the end-effector on the right arm 4 may be gripper capable of griping the tissue.

As illustrated, an endoscopic camera 2 passes through the upper channel and the bottom channel and may be used for using other device, like a third robotic arm for absorbing and injecting liquid. In some embodiments, the endoscopic platform may have at its tip an overtube with four holes, wherein the special shape of the holes are compatible to guide disks to smooth the translation and to restrict rotation of the robot arms.

Figure 3:
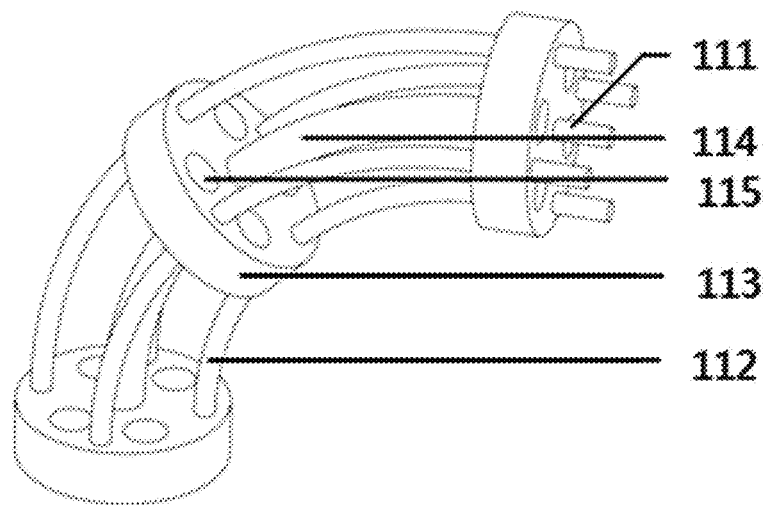
FIG. 3 is a schematic diagram illustrating a continuum structure.

FIG. 3 illustrates the detailed structure of the continuum structure 11. The continuum structure 11 comprises a backbone 111 configured to form a constant curvature, a plurality of (for example, two pairs as shown) actuators 112 extensible along formed constant curvature and configured to drive the end-effector, and a plurality of guide discs 113 separated from each other at a distance (e.g. by rubber spacers 114) and having holes 115 for receiving and guiding the actuators 112 and the backbone 111. In some embodiments, the material of the disks is, for example, 1.5 mm thick acrylic sheet, manufactured by laser machine. In order to achieve optimal curvature, the actuator-to-center ratio to spacer length can be set as, for example, 0.4. The four actuators are fixed at the tip of the continuum structure by using metal stoppers.

Figure 4:
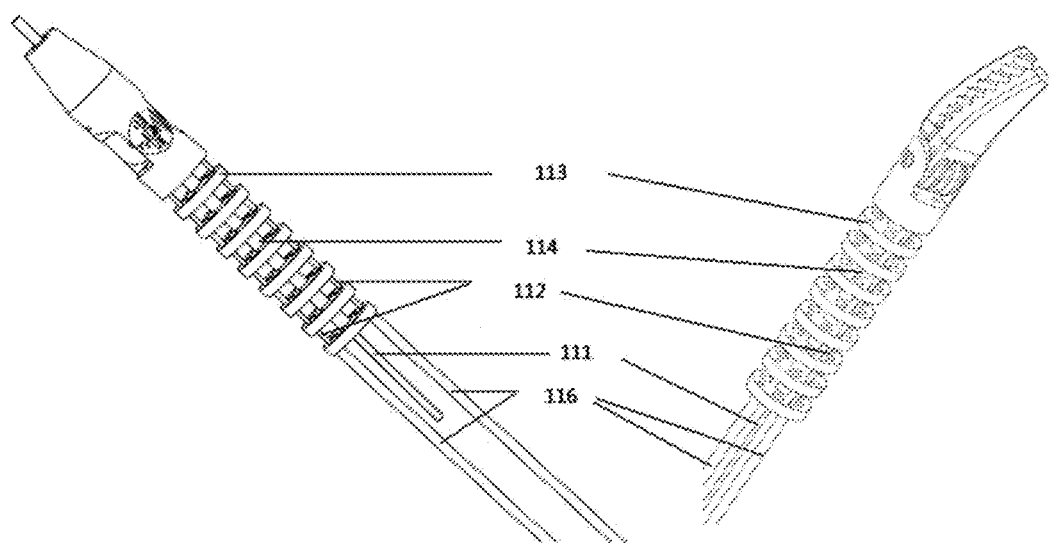
FIG. 4 is a schematic diagram illustrating two arms of the slave device.

In one embodiment, an electrocautery knife may be used as the backbone 111, as illustratively shown in FIG. 4. In this embodiment, each of the actuators 112 is formed by at least one of shape memory alloy and coated metal wire, and is received in a coil sheath 116, as shown in FIG. 4. These sheaths 116 are connected between the continuum structure and end-effector through a flexible channel. This tendon-sheath driving mechanism not only offers the flexibility requirement for endoscopic use, but also serves as a force turning mechanism.

The continuum structure 11 is actuated by two pairs of super elastic Ni—Ti shape memory alloy (SMA) wires, and the other joints, such as hinge joints and jaws, are driven by metal wires. By a combination of pushing and pulling movement of the four actuators 112 according to inverse kinemics, the tip of continuum structure can be precisely controlled. The superplastic property of SMA forces the continuum structure 111 to form a constant curvature, which can be precisely modeled and therefore, facilities to precisely control the position of its end-effector. On the other hand, compared with SMA, metal wires can form severe turning angle and can be fixed inside the guiding groove on gripper.

Such a continuum robotic mechanism fulfils the flexibility, dexterity and triangulation requirement for endoluminal operation. Forward and back translation can increase robotic arm's workspace, which is achieved by pushing and pulling the backbone 111 of the continuum structure 11. The bending and orientation of the continuum structure is achieved by pushing and pulling the two pair of actuators 112. The articulated heads (i.e., a gripper being able to change open direction and a hinge being able to change cutter direction) of both arms enable the robot to work on both vertical and horizontal plane to perform tissue lifting and dissection.

With the push-pull mechanism, at least two motors are needed for four actuators continuum robot. The relation between the curvature, rotation angle and the actuator length of three actuators continuum robot is as below:

$$\begin{bmatrix} l_1 \\ l_2 \\ l_3 \end{bmatrix} = \begin{bmatrix} s(1 - \kappa d \sin\phi) \\ s\left(1 + \kappa d \sin\left(\frac{\pi}{3} + \phi\right)\right) \\ s\left(1 - \kappa d \cos\left(\frac{\pi}{6} + \phi\right)\right) \end{bmatrix}$$

where $l_i$ is the length of ith actuator, s is the length of the backbone, $\kappa$ is the curvature of the continuum robot, d is the distance between actuator and backbone, and $\varphi$ is the rotation angle of the continuum robot.

Figure 5:
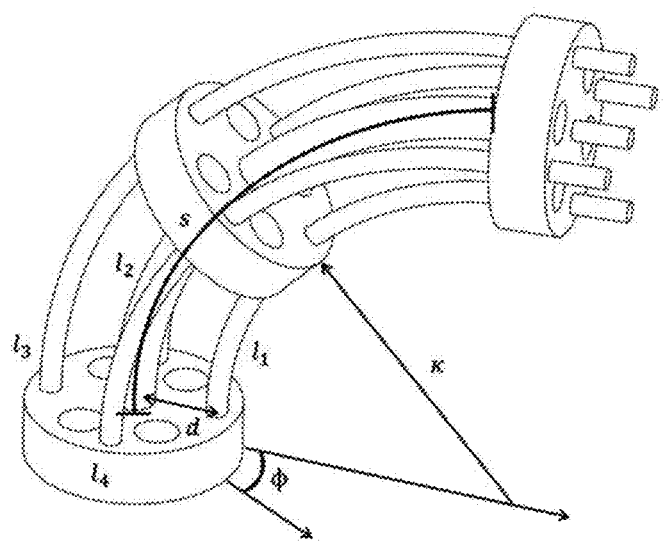
FIG. 5 is a schematic diagram illustrating the notation of parameters of the continuum structure.

The kinematics for four actuators case can be obtained by modifying the above equation. The structure is shown in FIG. 5. The angle between each actuator changed from 120 degree to 90 degree. The equation becomes:

$$\begin{bmatrix} l_1 \\ l_2 \\ l_3 \\ l_4 \end{bmatrix} = \begin{bmatrix} s(1 - \kappa d \sin\phi) \\ s\left(1 - \kappa d \sin\left(\frac{\pi}{2} + \phi\right)\right) \\ s(1 - \kappa d \sin(\pi + \phi)) \\ s\left(1 - \kappa d \sin\left(\frac{3\pi}{2} + \phi\right)\right) \end{bmatrix}$$

$$= \begin{bmatrix} s(1 - \kappa d \sin\phi) \\ s(1 + \kappa d \cos\phi) \\ s(1 + \kappa d \sin\phi) \\ s(1 - \kappa d \cos\phi) \end{bmatrix}$$

This yield $$s = \frac{l_1 + l_2 + l_3 + l_4}{4}$$

$$l_1 + l_3 = l_2 + l_4 = 2s$$

$$\Delta l_1 = -\Delta l_3, \Delta l_2 = -\Delta l_4$$

Due to these relations, $l_1$ and $l_3$ can be actuated by a push-pull driving unit and $l_2$ and $l_4$ can be actuated by another driving unit.

How the distance between each disk will be optimized has been proposed in the prior art. The distance from the backbone to actuator and the distance between disks have a ratio of 0.4. For the robot of the present application, the distance from backbone to actuator may be, for example, 2 mm. Therefore, the distance between discs may be, for example, 5 mm. This ratio provides less than 10% constant curvature model error without limiting the contact limit so much. Constant curvature modeling is used in the above equation.

Figure 6:
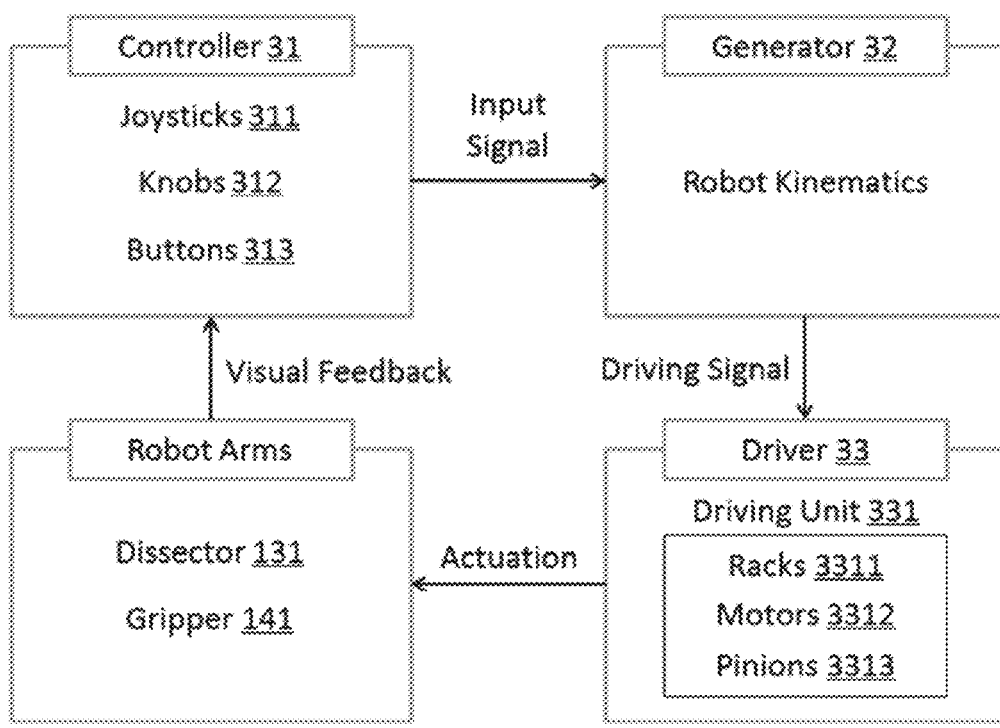
FIG. 6 is a block diagram illustrating a operation between the master device and the robot arms.

FIG. 6 is a block diagram illustrating an operation between the master device and the robotic arms. The master device 3 comprises a controller 31 configured to convert each action of a user into an input signal, a generator 32 configured to receive the input signal from the controller and generate a drive signal from the input signal, and a driver 33 configured to drive the slave robot according to the generated drive signal. In this embodiment, a visual feedback is used to control the robot through the controller. In some embodiments, other types of feedbacks are also possible.

Figure 7:
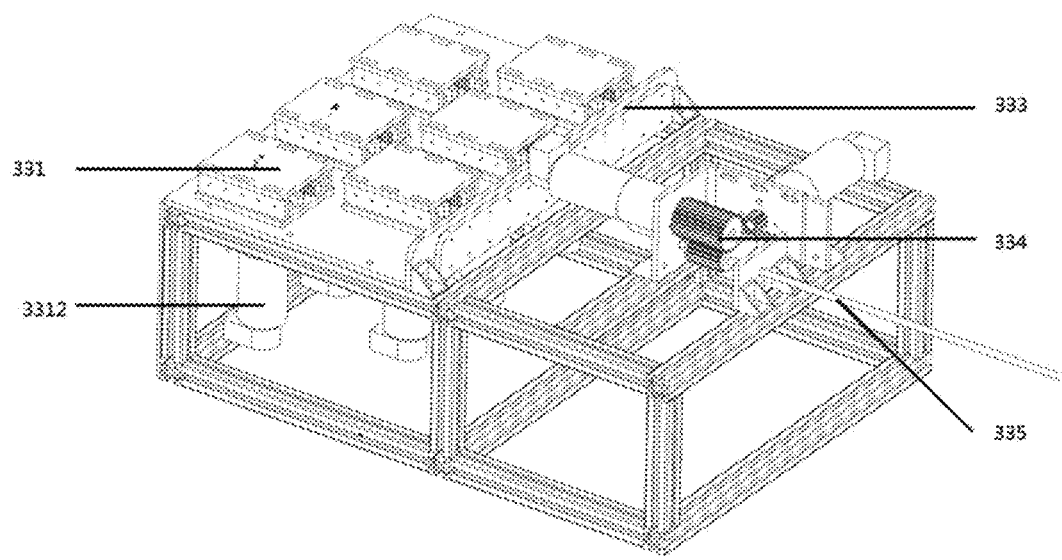
FIG. 7 is a schematic diagram illustrating a driver.
Figure 8:
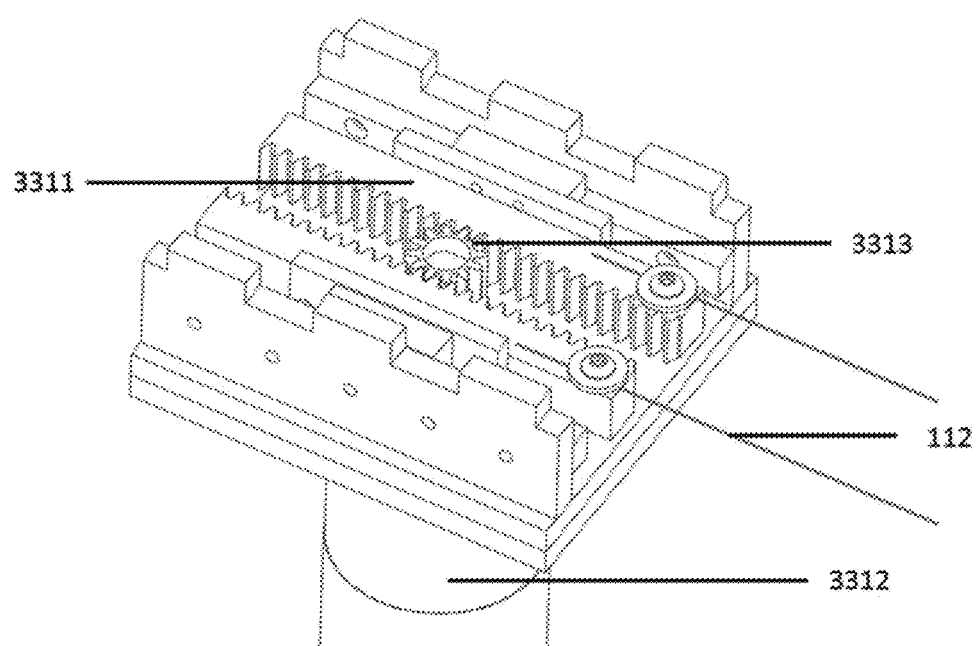
FIG. 8. is a schematic diagram illustrating a driving unit.
Figure 9:
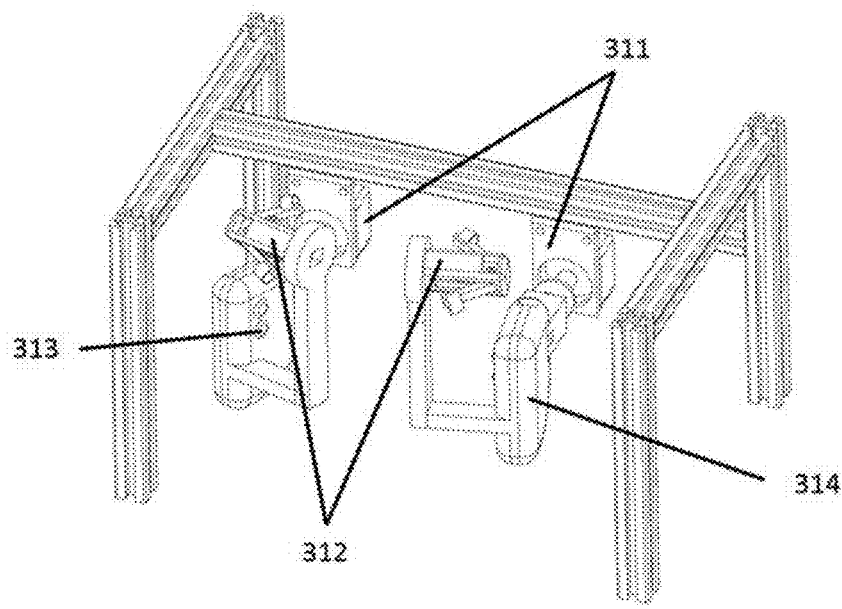
FIG. 9. is a schematic diagram illustrating a controller.

FIG. 7 is a schematic diagram illustrating a driver 33 having several driving units 331, and FIG. 8 is a schematic diagram illustrating a driving unit 331. Each driving unit contains a pair of opposite linear racks 3311 configured to fasten one pair of actuators, a motor 3312, and a pinion 3313 engaged between the two racks and driven by the motor to move the racks in different directions. In some embodiments, the driving unit 331 may comprise a motor controller. All sheaths are fixed on a stopping plane 333, while actuators can pass through the stopping plane and finally are fixed on the linear racks 3311. Actuators and backbone are passed through a flexible instrument shaft 335 before connected to the linear rack 3311 separately. Therefore, the translation mechanism 334 is achieved by translating the shaft as a whole. Bears are added between the linear rack and its sliding track to reduce friction. Through inverse kinematic calculation, two motors 3312 with 2 pairs of antagonized actuators can control the two degree of freedom of a continuum structure. With this driving mechanism, the left arm 13 has at least 4 degrees-of-freedom of movements, one for translation, two degrees-of-freedom that form a continuum structure for orientation and bending, and one degree-of-freedom that control its heading direction in vertical plane, while the right arm 14 has at least 5 degrees-of-freedom of movements, one for translation, two degrees-of-freedom that form a continuum structure for orientation and bending, and two degrees-of-freedom that respectively control the lower and upper jaws of the retractor.

FIG. 8 is a schematic diagram illustrating a controller. The controller consists of a joystick 311, a rotational knob 312, two control buttons 313, and a holding handle 314. A joint-to-joint mapping control strategy is used between the master and slave devices. The joystick with two degree-of-freedom is implemented to control the continuum structure 11. The rotational knob 312 with two degree-of-freedom controls the rotation and open angle of the gripper simultaneously. The two control buttons 313 controls the forward and backward translation motions of the first and second arms, respectively. Each joint position is measured by resistance position sensors. In some embodiment, a micro controller (for example, Arduino micro controller) can be used to sample the signals and communicate with the control software through series port.

Figure 10:
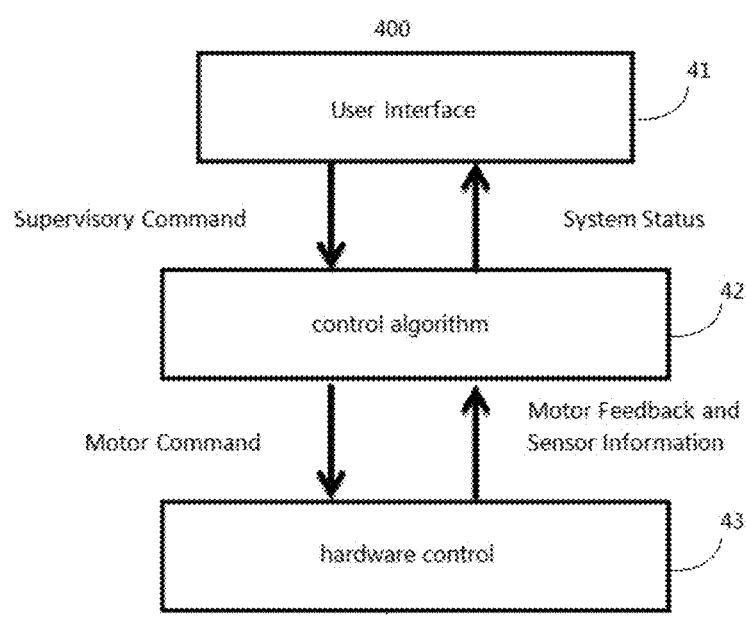
FIG. 10. is a schematic diagram illustrating a control software architecture.

The control software runs on a window based computer and is implemented by a hierarchical architecture shown in FIG. 10. The control software 400 may work in a hierarchy manner with 3 layers (from up to bottom): a user interface layer 41, a control algorithm layer 42, and a hardware control layer 43. Through this user interface, operator can adjust the parameters (home position, range) for each motor, calibrate the master's sensor and give supervisor command, like stop, start, and resetting system. A remote device with a multiple-layered configuration allows the users to precisely control the robotic arms. On the bottom layer, the motor motion control and master angular position sensor reading are realized. In addition, motors with different gear ratio are normalized on this layer in order to hide the hardware difference to GUI users. The major control algorithm and robotic modeling is implemented on the middle layer. It is responsible for trajectory generation, converting task space position to actuators' position by using inverse kinematics and keeping a recording of system status. On the top layer, it is the graphical user interface which can manage the input and output of the system. The input is supervisory command from the user which includes motor homing, home position resetting and etc. The output includes motor status that display for monitoring.

It is appreciated for those skilled in the art, with replacing the end-effectors with other dedicated tools, this robot can also be used for other endoscopic procedures, for example, biopsy taking and saline inject, as well as in other technical field, for example, in industrial field for checking and repairing the defects within industrial pipes.

Although the preferred examples of the present invention have been described, those skilled in the art can make variations or modifications to these examples upon knowing the basic inventive concept. The appended claims is intended to be considered as comprising the preferred examples and all the variations or modifications fell into the scope of the present invention.

Obviously, those skilled in the art can make variations or modifications to the present invention without departing the spirit and scope of the present invention. As such, if these variations or modifications belong to the scope of the claims and equivalent technique, they may also fall into the scope of the present invention.

What is claimed is:

1. A robot for Endoscopic Submucosal Dissection (ESD), comprising:
   a slave device configured with a first arm and a second arm;
   an endoscopic platform with at least two channels extensible to a target tissue and for receiving the first and second arms, respectively; and
   a master device configured to control the first arm to retract the target tissue and control the second arm to dissect the retracted tissue;
   each of the first arm and the second arm comprising a continuum structure and an end-effector connected with the continuum structure; and
   the continuum structure of the first and second arms comprising at least two pairs of actuators configured to drive the end-effector, the actuators in the first arm comprising a wire and a shape memory alloy, the wire and the shape memory alloy in the actuators of the first arm being separately controlled, and being used to control the end-effector and the first arm.

2. The robot of claim 1, wherein the continuum structure of the first arm and the continuum structure of the second arm are identical.

3. The robot of claim 2, wherein the continuum structure of the first and second arms comprises:
   a backbone configured to form a curve, the at least two pairs of actuators being extensible along the formed curve; and
   a plurality of guide discs separated from each other at a distance and having holes for receiving the actuators.

4. The robot of claim 3, wherein each of the actuators comprises a coated metal wire.

5. The robot of claim 4, wherein the slave device further comprises a third arm for absorbing and injecting liquid.

6. The robot of claim 4, wherein each of the actuators is arranged inside a sheath.

7. The robot of claim 6, wherein the sheaths are kept as a bundle and fixed inside a rubber tube.

8. The robot of claim 6, wherein the sheaths are connected between the continuum structure and the end-effector through a flexible channel.

9. The robot of claim 8, wherein the end effector on the first arm is a gripper, and the end effector on the second arm is a dissector.

10. The robot of claim 9, wherein the first arm has at least 5 degrees of freedom.

11. The robot of claim 9, wherein the second arm has at least 4 degrees of freedom.

12. The robot of claim 9, wherein the master device further comprises:
    a controller configured to convert each action of a user into an input signal;
    a generator configured to receive the input signal from the controller and generate a drive signal from the input signal; and
    a driver configured to drive the slave device according to the generated drive signal.

13. The robot of claim 12, wherein the controller comprises:
    a joystick configured to change an orientation of the continuum structure;
    a rotation knob configured to control a rotation and open angle of the gripper; and
    control buttons configured to control forward and backward translation motions of the first and second arms.

14. The robot of claim 13, wherein an electrocautery knife is used as the backbone.

15. The robot of claim 12, wherein the driver comprises at least one driving unit for driving the actuators, each driving unit comprising:
    two racks configured to fasten one pair of actuators;
    a motor; and
    a pinion engaged between the two racks and driven by the motor to move the racks in different directions.

16. A robot for Endoscopic Submucosal Dissection (ESD), comprising:
    a first arm;
    a second arm; and
    an endoscopic platform with at least two channels extensible to a target tissue and for receiving the first and second arms, respectively,
    the first arm being configured to retract the target tissue and the second arm being configured to dissect the retracted tissue,
    each of the first arm and the second arm comprising a continuum structure and an end-effector connected with the continuum structure, and
    the continuum structure of the first and second arms comprising at least two pairs of actuators configured to drive the end-effector, the actuators in the first arm comprising a wire and a shape memory alloy, the wire and the shape memory alloy in the actuators of the first arm being separately controlled, and being used to control the end-effector and the first arm.

17. The robot of claim 16, wherein the continuum structure of the first arm and the continuum structure of the second arm are identical, and wherein the continuum structure is flexible to guide the end-effector to the target tissue.

18. The robot of claim 17, wherein the continuum structure of the first and second arms comprises:
  a backbone for forming a curve, the at least two pairs of actuators being extensible along formed curve; and
  a plurality of guide discs separated from each other at a distance and having holes for receiving the actuators.

19. The robot of claim 18, wherein the end effector on the first arm is a gripper, and the end effector on the second arm is a dissector.

20. The robot of claim 19, wherein each of the actuators is received in a sheath.

21. The robot of claim 20, wherein the sheaths are kept as a bundle and fixed inside a rubber tube.

\* \* \* \* \*